US010226438B2

(12) United States Patent
Scanlan et al.

(10) Patent No.: US 10,226,438 B2
(45) Date of Patent: Mar. 12, 2019

(54) SOBETIROME IN THE TREATMENT OF MYELINATION DISEASES

(71) Applicants: Thomas S. Scanlan, San Francisco, CA (US); Meredith Hartley, Portland, OR (US); Andrew Placzek, Portland, OR (US); Marco Righi, Rosignano (IT); Dennis Bourdette, Portland, OR (US); Gail Marracci, Portland, OR (US); Priya Chaudhary, Portland, OR (US)

(72) Inventors: Thomas S. Scanlan, San Francisco, CA (US); Meredith Hartley, Portland, OR (US); Andrew Placzek, Portland, OR (US); Marco Righi, Rosignano (IT); Dennis Bourdette, Portland, OR (US); Gail Marracci, Portland, OR (US); Priya Chaudhary, Portland, OR (US)

(73) Assignees: Oregon Health & Science University, Portland, OR (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/888,577

(22) PCT Filed: Feb. 5, 2014

(86) PCT No.: PCT/US2014/014943
§ 371 (c)(1),
(2) Date: Nov. 2, 2015

(87) PCT Pub. No.: WO2014/178931
PCT Pub. Date: Nov. 6, 2014

(65) Prior Publication Data
US 2016/0081955 A1    Mar. 24, 2016

Related U.S. Application Data (63) Continuation-in-part of application No. PCT/US2013/053640, filed on Aug. 5, 2013.

(60) Provisional application No. 61/819,467, filed on May 3, 2013.

(51) Int. Cl.
*A61K 31/192* (2006.01)
*A61P 25/14* (2006.01)
*A61K 9/00* (2006.01)

(52) U.S. Cl.
CPC .......... *A61K 31/192* (2013.01); *A61K 9/0053* (2013.01); *A61K 9/0095* (2013.01)

(58) Field of Classification Search
CPC ........ A61K 31/19; A61K 31/192; A61P 25/14
USPC ........................................................ 514/571
See application file for complete search history.

(56) References Cited

U.S. PATENT DOCUMENTS

| | | |
|---|---|---|
| 5,883,294 A | 3/1999 | Scanlan et al. |
| 6,054,485 A | 4/2000 | Schwartz et al. |
| 6,107,517 A | 8/2000 | Scanlan et al. |
| 6,236,946 B1 | 5/2001 | Scanlan et al. |
| 7,302,347 B2 | 11/2007 | Baxter et al. |
| 2003/0215434 A1 | 11/2003 | Khan et al. |
| 2008/0124280 A1 | 5/2008 | Mousa et al. |
| 2009/0306225 A1 | 12/2009 | Lichter et al. |
| 2010/0303934 A1 | 12/2010 | Soumyanath et al. |
| 2011/0178134 A1* | 7/2011 | Jaehne ............. C07D 401/06 514/341 |
| 2012/0004166 A1 | 1/2012 | Keil et al. |

FOREIGN PATENT DOCUMENTS

| | | |
|---|---|---|
| WO | WO 2006/031922 | 3/2006 |
| WO | WO 2008/125724 | 10/2008 |
| WO | WO 2014/178892 A1 | 11/2014 |
| WO | WO 2014/178931 A1 | 11/2014 |

OTHER PUBLICATIONS

Meinig, ACS Chem. Neurosci., DOI: 10.1021/acschemneuro.7b00239 Publication Date (Web): Jul. 30, 2017.*
Placzek, Bioorganic & Medicinal Chemistry 24 (2016) 5842-5854.*
D'Intino et al. Journal of Neuroendocrinology, 2011, vol. 23, pp. 778-790 (Year: 2011).*
Dell'Acqua et al. Neuropathology and Applied Neurobiology, 2012, vol. 38, pp. 454-470 (Year: 2012).*
Baxter et al., "Selective Modulation of Thyroid Hormone Receptor Action," *J. Steroid Biochem. Mol. Bio.*, vol. 76:31-42, 2001.
Fourcade et al., "Thyroid Hormone Induction of the Adrenoleukodystrophy-Related Gene (ABCD2)," *Mol. Pharmacol.*, vol. 63:1296-1303, 2003.
Hafer-Macko et al., "Immune Attack on the Schwann Cell Surface in Acute Inflammatory Demyelinating Polyneuropathy," *Ann. Neurol.*, vol. 39:625-635, 1996.
Miller et al., "Primary-Progressive Multiple Sclerosis," *Lance Neurol.*, vol. 6:903-912, 2007.
Scanlan, "Safety and Pharmacodynamic Study of Sobetirome in X-Linked Adrenoleukodystrophy (X-ALD)," available online at ClinicalTrials.gov on Feb. 6, 2013, 3 pages (clinicaltrials.gov/ct2/show/NCT01787578?term=Scanlan&rank=1).
Scanlan, "Sobetirome: a case history of bench-to-clinic drug discovery and development," *Heart Fail Rev* 15:177-182, 2010.
Genin et al., "Induction of adrenoleukodystrophy-related gene (ABCD2) by thyromimetics," *J Steroid Biochem Mol Biol* 116(1-2):37-43, 2009.
U.S. Department of Health and Human Services, Health Resources and Services Administration (HRSA), "Orphan Drug Designations and Approvals List as of Sep. 3, 2013," retrieved on Jan. 24, 2014 from http://www.hrsa.gov/opa/programrequirements/orphandrugexclusion/ (253 pages; p. 45).

(Continued)

Primary Examiner — James D. Anderson
(74) Attorney, Agent, or Firm — Klarquist Sparkman, LLP (57) ABSTRACT

Methods of treating a subject having or at risk of developing a neurodegenerative disease or condition associated with demyelination, insufficient myelination, or underdevelopment of myelin sheath are described. The methods include administration of a therapeutically effective amount of sobetirome, or a pharmaceutically acceptable salt thereof.

6 Claims, 4 Drawing Sheets

(56) References Cited

OTHER PUBLICATIONS

Engelen et al., "X-linked adrenoleukodystrophy (X-ALD): clinical presentation and guidelines for diagnosis, follow-up and management," *Orphanet Journal of Rare Diseases* 7:51, 2012 (14 pages).
Johnson, "Demyelinating Diseases," in The Infectious Etiology of Chronic Diseases: Defining the Relationship, Enhancing the Research and Mitigating the Effects: Workshop Summary, Knobler SL, O'Connor S, Lemon SM et al. editors, Washington, D.C, National Academies Press (US), 2004, pp. 45-52.

* cited by examiner

SOBETIROME IN THE TREATMENT OF MYELINATION DISEASES

CROSS REFERENCE TO RELATED APPLICATIONS

This is the U.S. National Stage of International Application No. PCT/US2014/014943, filed Feb. 5, 2014, published in English under PCT Article 21(2), which claims the benefit of international application PCT/US2013/053640, filed on Aug. 5, 2013; and claims the benefit of U.S. Provisional Application 61/819,467, filed on May 3, 2013, the disclosures of each of which are incorporated herein by reference.

ACKNOWLEDGMENT OF GOVERNMENT SUPPORT

This invention was made with government support under grant number DK-52798 awarded by the National Institutes of Health. The government has certain rights in the invention.

PARTIES TO JOINT RESEARCH AGREEMENT

The inventions described in this application were made by Oregon Health & Sciences University and The United States Government as represented by the Department of Veterans Affairs as a result of activities undertaken within the scope of a joint research agreement.

FIELD

This disclosure concerns methods for the treatment of diseases or conditions associated with demyelination, insufficient myelination or underdevelopment of the myelin sheath. This disclosure further relates to the use of sobetirome for the treatment of such diseases and conditions.

BACKGROUND

Oligodendrocytes (OL) generate and maintain myelin in the central nervous system (CNS). During development, oligodendrocyte precursor cells (OPC) differentiate into OL and this differentiation step depends on the thyroid hormone, triiodothyronine (T3). Following demyelination, remyelination may involve T3-dependent differentiation of OPC into OL, which depends on transcription factors, e.g., Kruppel-like factor 9 (Klf9). Currently available treatments of demyelinating diseases are limited in their efficacy. For some demyelinating diseases, there are no known treatments available. Thus, therapeutic agents capable of promoting remyelination, without toxic side effects, represent an unmet medical need.

SUMMARY

The present disclosure features the use of a CNS active, non-cardiotoxic drug (sobetirome) capable of reducing demyelination and promoting myelination without causing thyrotoxicosis. Sobetirome, and pharmaceutically acceptable salts thereof, provide a viable treatment for preventing and reversing demyelination in disorders such as multiple sclerosis (MS) and other diseases or conditions associated with demyelination, insufficient myelination, or underdevelopment of the myelin sheath.

Methods of treating a subject having or at risk of developing a neurodegenerative disease or condition associated with demyelination, insufficient myelination, or underdevelopment of myelin sheath are described herein. The methods include administration of a therapeutically effective amount of sobetirome, or a pharmaceutically acceptable salt thereof.

The foregoing and other objects, features, and advantages of the invention will become more apparent from the following detailed description, which proceeds with reference to the accompanying figures.

BRIEF DESCRIPTION OF THE DRAWINGS

FIG. 1: Sobetirome reduced demyelination in the corpus callosum of mice following injection of lysolecithin. Top. BlackGold® stain is specific for myelin fibers and cresyl violet is used as a counterstain. Mice received stereotactic injections of 2 μL of PBS or 2% lysolecithin in the corpus callosum. A white arrow indicates the path of the injection needle and a black box indicates the lesion site. An enlarged image of the boxed lesion site is shown to the right. Bottom, brain sections of 30 μm were stained with FluoroMyelin™, anti-PDGFR-α and DAPI. Hypothyroidism was induced with drinking water treatment, and both hypothyroid and control mice received vehicle injections. T3 (0.4 mg/kg) and sobetirome (1 mg/kg) were administered by daily i.p. injections starting 7 days before stereotactic injection of lysolecithin. Mice were euthanized 8 days after stereotactic injection of 2% lysolecithin, and brains were harvested and processed for histological analysis.

DETAILED DESCRIPTION

I. Abbreviations

ADEM acute disseminated encephalomyelitis
AIDP acute inflammatory demyelinating polyneuropathy
CIDP chronic inflammatory demyelinating polyneuropathy
CNS central nervous system
EAE experimental autoimmune encephalitis
IIDD idiopathic inflammatory demyelinating disease
i.p. intraperitoneal
MOG myelin oligodendrocyte glycoprotein
MS multiple sclerosis
NMO neuromyelitis optica
OL oligodendrocytes
OPC oligodendrocyte precursor cells PML progressive multifocal leukoencephalopathy
T3 triiodothyronine
X-ALD X-linked adrenoleukodystrophy

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Acute disseminated encephalomyelitis (ADEM): An immune-mediated demyelinating disease of the central nervous system. ADEM usually occurs following a viral infection, but may also appear following vaccination or following bacterial or parasitic infection. In some cases, ADEM develops spontaneously. The disease involves autoimmune demyelination, similar to multiple sclerosis, and is therefore considered a multiple sclerosis borderline disease. ADEM produces multiple inflammatory lesions in the brain and spinal cord, particularly in the white matter. The lesions are typically found in the subcortical and central white matter and cortical gray-white junction of both cerebral hemispheres, cerebellum, brainstem, and spinal cord, but periventricular white matter and gray matter of the cortex, thalami and basal ganglia may also be involved. When a patient suffers more than one demyelinating episode, the disease is referred to as recurrent disseminated encephalomyelitis or multiphasic disseminated encephalomyelitis.

Acute hemorrhagic leukoencephalitis (AHL or AHLE): A hyperacute and frequently fatal form of ADEM. This disease is also known as acute necrotizing encephalopathy (ANE), acute hemorrhagic encephalomyelitis (AHEM), acute necrotizing hemorrhagic leukoencephalitis (ANHLE), Weston-Hurst syndrome, or Hurst's disease.

Administration: To provide or give a subject an agent, such as a therapeutic agent (e.g. sobetirome or a pharmaceutically acceptable salt thereof), by any effective route. Exemplary routes of administration are described hereinbelow.

Adult Refsum disease: An autosomal recessive neurological disease that is associated with the over-accumulation of phytanic acid in cells and tissues. Adult Refsum disease is divided into the adult Refsum disease 1 and adult Refsum disease 2 subtypes. Individuals with Refsum disease present with neurologic damage, cerebellar degeneration, and peripheral neuropathy. Onset is most commonly in childhood/adolescence with a progressive course, although periods of stagnation or remission occur. Symptoms also include ataxia, scaly skin (ichthyosis), difficulty hearing, and eye problems including cataracts and night blindness.

Alexander disease: A very rare, congenital demyelinating disease. The disease primarily affects infants and children, causing developmental delay and changes in physical characteristics. Alexander disease is a type of leukodystrophy.

Alzheimer's disease: The most common form of dementia. Symptoms of Alzheimer's disease include memory loss, confusion, irritability, aggression, mood swings and trouble with language. This disease is characterized by the loss of neurons and synapses in the cerebral cortex and certain subcortical regions. The loss results in gross atrophy of the affected regions, including degeneration in the temporal lobe, and parts of the frontal cortex and cingulate gyrus. Amyloid plaques and neurofibrillary tangles are visible by microscopy in brains of those afflicted with this disease. The cause of Alzheimer's disease is unknown; however, several hypothesis exist, including that the disease is caused by age-related myelin breakdown in the brain.

Balo concentric sclerosis: A demyelinating disease similar to standard multiple sclerosis, but with the particularity that the demyelinated tissues form concentric layers. Patients with this disease can survive and/or have spontaneous remission. Typically, the clinical course is primary progressive, but a relapsing-remitting course has been reported.

Canavan disease: An autosomal recessive degenerative disorder that causes progressive damage to nerve cells in the brain. Canavan disease is a leukodystrophy and is one of the most common degenerative cerebral diseases of infancy. This disease is also called Canavan-Van Bogaert-Bertrand disease, aspartoacylase deficiency and aminoacylase 2 deficiency.

Central pontine myelinolysis (CPM): A neurologic disease caused by severe damage of the myelin sheath of nerve cells in the brainstem, more precisely in the area termed the pons. The most common cause is the rapid correction of low blood sodium levels (hyponatremia). Frequently observed symptoms in this disorder are sudden para or quadraparesis, dysphagia, dysarthria, diplopia and loss of consciousness. The patient may experience locked-in syndrome where cognitive function is intact, but all muscles are paralyzed with the exception of eye blinking.

Cerebral palsy: A term used for a group of permanent, non-progressive movement disorders that cause physical disability. Cerebral palsy is caused by damage to the motor control centers of the developing brain and can occur during pregnancy, during childbirth, or after birth up to about age three. Patients with cerebral palsy exhibit damage to myelin sheaths.

Cerebrotendineous xanthomatosis: An inherited disorder associated with the deposition of a form of cholesterol (cholestanol) in the brain and other tissues and with elevated levels of cholesterol in plasma but with normal total cholesterol level. It is characterized by progressive cerebellar ataxia beginning after puberty and by juvenile cataracts, juvenile or infantile onset chronic diarrhea, childhood neurological deficit, and tendineous or tuberous xanthomas. This disorder is an autosomal recessive form of xanthomatosis. It falls within a group of genetic disorders called the leukodystrophies.

Chronic inflammatory demyelinating polyneuropathy (CIDP): An acquired immune-mediated inflammatory disorder of the peripheral nervous system. The disorder is sometimes called chronic relapsing polyneuropathy (CRP) or chronic inflammatory demyelinating polyradiculoneuropathy (because it involves the nerve roots). CIDP is closely related to Guillain-Barré syndrome and it is considered the chronic counterpart of that acute disease. Its symptoms are also similar to progressive inflammatory neuropathy. An asymmetrical variant of CIDP is known as Lewis-Sumner syndrome. The pathologic hallmark of the disease is loss of the myelin sheath.

Demyelinating disease: Includes any disease of the nervous system in which myelin is damaged or lost, or in which the growth or development of the myelin sheath is impaired. Demyelination inhibits the conduction of signals in the affected nerves, causing impairment in sensation, movement, cognition, or other functions for which nerves are involved. Demyelinating diseases have a number of different causes and can be hereditary or acquired. In some cases, a demyelinating disease is caused by an infectious agent, an autoimmune response, a toxic agent or traumatic injury. In other cases, the cause of the demyelinating disease is unknown ("idiopathic") or develops from a combination of factors.

Devic's syndrome: An autoimmune, inflammatory disorder in which a person's immune system attacks the optic nerves and spinal cord, which results in inflammation of the optic nerve (optic neuritis) and the spinal cord (myelitis). Spinal cord lesions lead to varying degrees of weakness or paralysis in the legs or arms, loss of sensation, and/or bladder and bowel dysfunction. Although inflammation may also affect the brain, the lesions are different from those observed in MS. Devic's disease is similar to MS in that the body's immune system attacks the myelin surrounding nerve cells. Unlike standard MS, the attacks are not believed to be mediated by the immune system's T cells but rather by antibodies called NMO-IgG. These antibodies target a protein called aquaporin 4 in the cell membranes of astrocytes which acts as a channel for the transport of water across the cell membrane. Devic's syndrome is also known as Devic's disease or neuromyelitis optica (NMO).

Diffuse myelinoclastic sclerosis: An uncommon neurodegenerative disease that presents clinically as pseudotumoral demyelinating lesions. It usually begins in childhood, affecting children between 5 and 14 years old; however, cases in adults are possible. This disease is considered one of the borderline forms of MS and is sometimes referred to as Schilder's disease.

Encephalomyelitis: Inflammation of the brain and spinal cord.

Experimental autoimmune encephalomyelitis (EAE): An animal model of MS (for example, see Gold et al., *Brain* 129:1953-1971, 2006). EAE animals exhibit characteristic plaques of tissue injury disseminated throughout the central nervous system. Plaques show infiltration of nervous tissue by lymphocytes, plasma cells, and macrophages, which cause destruction of the myelin sheaths that surround nerve cell axons in the brain and spinal cord. In some cases. EAE is induced by immunization of susceptible animals, such as mice, rats, guinea pigs, or non-human primates, with either myelin or various components of myelin. For example, EAE can be induced by immunization with components of the myelin sheath, such as myelin basic protein, proteolipid protein, or myelin oligodendrocyte glycoprotein (MOG). EAE is a useful and widely accepted model for studying mechanisms of autoimmune CNS tissue injury and for testing potential therapies for MS. EAE also includes "passive EAE" which is induced in the same manner in donor animals, but involves the transfer of activated T-cells harvested from the donor animal's lymph nodes to naïve recipient animals.

Guillain-Barré syndrome: An acute polyneuropathy, a disorder affecting the peripheral nervous system. Ascending paralysis, weakness beginning in the feet and hands and migrating towards the trunk, is the most typical symptom, and some subtypes cause change in sensation or pain, as well as dysfunction of the autonomic nervous system. It can cause life-threatening complications, in particular if the respiratory muscles are affected or if the autonomic nervous system is involved. This disease is usually triggered by an infection. Acute inflammatory demyelinating polyneuropathy (AIDP) is the most common subtype of this disease. Other subtypes of Guillain-Barré syndrome include Miller Fischer syndrome, acute motor axonal neuropathy (Chinese paralytic syndrome), acute motor sensory axonal neuropathy, acute panautonomic neuropathy, and Bickerstaff's brainstem encephalitis.

Hemorrhage: Bleeding or escape of blood from a vessel.

Hypoxia: The lack of oxygen supply to the tissues of the body below the normal level.

Idiopathic inflammatory demyelinating disease (IIDD): A broad spectrum of central nervous system disorders that can usually be differentiated on the basis of clinical, imaging, laboratory and pathological findings. Idiopathic inflammatory demyelinating diseases are sometimes known as borderline forms of multiple sclerosis. IIDD generally refers to a collection of multiple sclerosis variant diseases, including but not limited to, optic-spinal MS, Devic's disease, ADEM, acute hemorrhagic leukoencephalitis, Balo concentric sclerosis, Schilder disease, Marburg multiple sclerosis, tumefactive multiple sclerosis and solitary sclerosis.

Infantile Refsum disease: A peroxisome biogenesis disorder associated with deficiencies in the catabolism of very long chain fatty acids and branched chain fatty acids (such as phytanic acid) and plasmalogen biosynthesis. Infantile Refsum disease is a rare, autosomal recessive congenital disorder, and one of three peroxisome biogenesis disorders that belong to the Zellweger spectrum of peroxisome biogenesis disorders.

Injury: Refers to any type of physical damage to cells, tissues, or the body. In some cases, nervous system (e.g., CNS or PNS) injury results in demyelination and/or a demyelinating disease.

Ischemia: A vascular phenomenon in which a decrease in the blood supply to a bodily organ, tissue, or part is caused, for instance, by constriction or obstruction of one or more blood vessels. Ischemia sometimes results from vasoconstriction, thrombosis or embolism. Ischemia can lead to direct ischemic injury, tissue damage due to cell death caused by reduced oxygen supply. In some cases, ischemia can lead to demyelination.

Krabbe disease: A rare, often fatal degenerative disorder that affects the myelin sheath of the nervous system. It is a form of sphingolipidosis, as it involves dysfunctional metabolism of sphingolipids. This condition is inherited in an autosomal recessive pattern. Krabbe disease is also known as globoid cell leukodystrophy or galactosylceramide lipidosis.

Leber hereditary optic neuropathy: A mitochondrially inherited (transmitted from mother to offspring) degeneration of retinal ganglion cells (RGCs) and their axons that leads to an acute or subacute loss of central vision; this affects predominantly young adult males.

Leukodystrophy: Refers to a group of diseases that affects the growth or development of the myelin sheath.

Leukoencephalopathy: Any of a group of diseases affecting the white substance of the brain; can refer specifically to several diseases including, for example, "leukoencephalopathy with vanishing white matter" and "toxic leukoencephalopathy." Leukoencephalopathies are leukodystrophy-like diseases.

Marburg multiple sclerosis: A condition in which the central nervous system has multiple demyelinating lesions with atypical characteristics for those of standard multiple sclerosis. This disease is a borderline form of multiple sclerosis and is also known as tumefactive multiple sclerosis or fulminant multiple sclerosis. It is called tumefactive because the lesions are "tumor-like" and they mimic tumors clinically, radiologically and sometimes pathologically.

Marchiafava-Bignami disease: A progressive neurological disease characterized by corpus callosum demyelination and necrosis and subsequent atrophy. It is classically associated with chronic alcoholics.

Metachromatic leukodystrophy (MLD): A lysosomal storage disease that is commonly listed in the family of leukodystrophies, as well as in the sphingolipidoses as it affects the metabolism of sphingolipids. MLD is directly caused by a deficiency of the enzyme arylsulfatase A.

Multifocal motor neuropathy (MMN): A progressively worsening condition where muscles in the extremities gradually weaken. This disorder, a motor neuropathy syndrome, is sometimes mistaken for amyotrophic lateral sclerosis (ALS) because of the similarity in the clinical picture, especially if muscle fasciculations are present. MMN is usually asymmetric and is thought to be autoimmune.

Multiple sclerosis (MS): A slowly progressive CNS disease characterized by disseminated patches of demyelination in the brain and spinal cord, resulting in multiple and varied neurological symptoms and signs, usually with remissions and exacerbation. The cause of MS is unknown but an immunological abnormality is suspected. An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary-progressive multiple sclerosis (PPMS) presents initially in the progressive form. A clinically isolated syndrome is the first neurologic episode, which is caused by inflammation/demyelination at one or more sites in the CNS. Progressive-relapsing multiple sclerosis (PRMS) is a rare form of MS (~5%) characterized by a steadily worsening disease state from onset, with acute relapses but no remissions.

Myelin: A lipid substance forming a sheath (known as the myelin sheath) around the axons of certain nerve fibers. Myelin is an electrical insulator that serves to speed the conduction of nerve impulses in nerve fibers. "Myelination" (also "myelinization") refers to the development or formation of a myelin sheath around a nerve fiber. Similarly, "remyelination" (also, "remyelinization") refers to the repair or reformation of the myelin sheath, such as following injury, exposure to a toxic agent, or an inflammatory response, or during the course of a demyelinating disease.

Neurodegenerative disease: Refers to any type of disease that is characterized by the progressive deterioration of the nervous system.

Neuropathy: A functional disturbance or pathological change in the peripheral nervous system. Axonal neuropathy refers to a disorder disrupting the normal functioning of the axons.

Paraproteinemic demyelinating polyneuropathy: A type of peripheral neuropathy characterized by auto antibodies directed against myelin associated glycoproteins (MAG). Anti-MAG antibodies inhibit the production of myelin, thereby leading to neuropathy.

Pelizaeus-Merzbacher disease (PMD): A rare central nervous system disorder in which coordination, motor abilities, and intellectual function are delayed to variable extents. The disease is one in a group of genetic disorders collectively known as leukodystrophies.

Peroneal muscular atrophy (PMA): A genetically and clinically heterogeneous group of inherited disorders of the peripheral nervous system characterized by progressive loss of muscle tissue and touch sensation across various parts of the body. This disease is also known as Charcot-Marie-Tooth disease (CMT), Charcot-Marie-Tooth neuropathy and hereditary motor and sensory neuropathy (HMSN).

Pharmaceutical composition: A composition containing sobetirome, or a pharmaceutically acceptable salt thereof, formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

Pharmaceutically acceptable salt: A salt of sobetirome which is, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free carboxylic acid group with a suitable base. Representative alkali or alkaline earth metal salts include sodium, lithium, potassium, calcium, magnesium, and the like, as well as nontoxic ammonium, primary ammonium, secondary ammonium, tertiary ammonium, or quaternary ammonium cations, including, but not limited to ammonium, tetramethylammonium, tetraethylammonium, methylammonium, dimethylammonium, trimethylammonium, triethylammonium, ethylammonium, and the like.

Pharmaceutically acceptable excipient (pharmaceutically acceptable carrier): Any ingredient other than sobetirome, or a pharmaceutically acceptable salt thereof (e.g., a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The pharmaceutically acceptable excipients or carriers useful for each specific mode of administration are described hereinbelow.

Preventing, treating or ameliorating a disease: "Preventing" refers to a prophylactic treatment or treatment that prevents one or more symptoms or conditions of a disease, disorder, or conditions described herein. Preventive treatment that includes administration of sobetirome, or a pharmaceutically acceptable salt thereof, or a pharmaceutical composition thereof, can be acute, short-term, or chronic. The doses administered may be varied during the course of preventative treatment. "Treating" refers to an approach for obtaining beneficial or desired results, e.g., clinical results. Beneficial or desired results can include, but are not limited to, alleviation or amelioration of one or more symptoms or conditions; diminishment of extent of disease or condition; stabilized (i.e., not worsening) state of disease, disorder, or condition; preventing spread of disease or condition; delay or slowing the progress of the disease or condition; amelioration or palliation of the disease or condition; and remission (whether partial or total), whether detectable or undetectable. "Ameliorating (palliating)" a disease or condition means that the extent and/or undesirable clinical manifestations of the disease, disorder, or condition are lessened and/or time course of the progression is slowed or lengthened, as compared to the extent or time course in the absence of treatment.

Progressive multifocal leukoencephalopathy (PML): A rare and usually fatal viral disease that is characterized by progressive damage or inflammation of the white matter of the brain in multiple locations. PML occurs almost exclusively in people with severe immune deficiency. The cause of PML is a type of polyomavirus called the JC virus. The virus is widespread, with 86% of the general population presenting antibodies, but it usually remains latent, causing disease only when the immune system has been severely weakened. PML is a demyelinating disease, in which the myelin sheath covering the axons of nerve cells is gradually destroyed, impairing the transmission of nerve impulses. The disease may occur in subjects (e.g., humans) with severe immune deficiency, such as transplant patients on immunosuppressive medications or those receiving certain kinds of medications. For example, PML has been associated with administration of rituximab (off-label use in the treatment of multiple sclerosis). It affects the white matter, which is mostly composed of axons from the outermost parts of the brain (cortex). Symptoms include weakness or paralysis, vision loss, impaired speech, and cognitive deterioration.

Sobetirome: A synthetic diarylmethane derivative that was investigated clinically as a potential therapeutic for hypercholesterolemia (see U.S. Pat. No. 5,883,294, which is herein incorporated by reference). Other names for sobetirome found in the literature and regulatory filings include QRX-431 and GC-1.

Subject: An animal (e.g., a mammal, such as a human). A subject to be treated according to the methods described herein may be one who has been diagnosed with a neurodegenerative disease involving demyelination, insufficient myelination, or under-development of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

Therapeutically effective amount: A quantity of sobetirome, or a pharmaceutically acceptable salt thereof, sufficient to achieve a desired effect in a subject, or in a cell, being treated with sobetirome. The effective amount of sobetirome depends on several factors, including, but not limited to the subject or cells being treated, and the manner of administration of the therapeutic composition. In some embodiments, a "therapeutically effective amount" of sobetirome, or a pharmaceutically acceptable salt thereof, is the amount sufficient to promote myelination in a subject. In other embodiments, a "therapeutically effective amount" of sobetirome, or a pharmaceutically acceptable salt thereof, is the amount sufficient to inhibit demyelination in a subject.

Transverse myelitis: A neurological disorder caused by an inflammatory process of the grey and white matter of the spinal cord, leading to axonal demyelination. Demyelination arises idiopathically following infections or vaccination, or due to multiple sclerosis. Symptoms include weakness and numbness of the limbs as well as motor, sensory, and sphincter deficits. Severe back pain may occur in some patients at the onset of the disease.

Tropical spastic paraparesis (TSP): An infection of the spinal cord by human T-lymphotropic virus resulting in paraparesis, weakness of the legs. TSP is also known as HTLV-associated myelopathy or chronic progressive myelopathy. As the name suggests, this disease is most common in tropical regions, including the Caribbean and Africa.

Van der Knaap disease: A form of hereditary CNS demyelinating disease. This disease is a type of leukodystrophy and is also known as megalencephalic leukoencephalopathy with subcortical cysts (MLC).

X-linked adrenoleukodystrophy (X-ALD, ALD, or X-linked ALD): A rare, inherited metabolic disorder that leads to progressive brain damage, mental deterioration, failure of the adrenal glands, muscle spasms, blindness and eventually death. ALD is one disease in a group of inherited disorders called leukodystrophies. Adrenoleukodystrophy progressively damages myelin. X-linked ALD male patients may be divided into 7 phenotypes: childhood cerebral (progressive neurodegenerative decline leading to a vegetative state), adolescent (similar to childhood cerebral form but with a slower progression), adrenomyeloneuropathy (progressive neuropathy, paraparesis, may progress to cerebral involvement), adult cerebral (dementia, similar progression to childhood cerebral form), olivo-ponto-cerebellar (cerebral and brain stem involvement), Addison disease (adrenal insufficiency), asymptomatic (no clinical presentation, subclinical adrenal insufficiency, or AMN phenotype). X-linked ALD female patients may be divided into 5 phenotypes: asymptomatic (no neurologic or adrenal involvement), mild myelopathy, moderate to severe myelopathy (similar to male AMN phenotype), cerebral (progressive dementia and decline), and adrenal (primary adrenal insufficiency). X-linked ALD patients may progress from one phenotype to another over the course of their life. ALD is also known as Addison-Schilder disease or Siemerling-Creutzfeldt disease.

Zellweger syndrome: A rare congenital disorder, characterized by the reduction or absence of functional peroxisomes in the cells of an individual. This disease is classified as a leukodystrophy and is one of three peroxisome biogenesis disorders that belong to the Zellweger spectrum of peroxisome biogenesis disorders.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

III. Overview of Several Embodiments

Sobetirome, or a pharmaceutically acceptable salt thereof, provides a viable treatment for preventing and reversing demyelination and/or promoting myelination in diseases or conditions associated with demyelination, insufficient myelination, or underdevelopment of the myelin sheath.

The present disclosure features a method of treating a subject having or at risk of developing X-linked adrenoleukodystrophy by administering to the subject in need thereof a therapeutically effective amount of sobetirome or a pharmaceutically acceptable salt thereof. The present disclosure also features a method of inhibiting accumulation of very-long chain fatty acids in a cell in a patient that has or is at risk of developing X-linked adrenoleukodystrophy, by contacting the neuron with sobetirome, or a pharmaceutically acceptable salt thereof.

In some embodiments, the phenotype of X-linked adrenoleukodystrophy is childhood cerebral, adolescent, adrenomyeloneuropathy, adult cerebral, olivo-ponto-cerebellar, Addison disease, or asymptomatic. In other embodiments, the phenotype of X-linked adrenoleukodystrophy is asymptomatic, mild myelopathy, moderate to severe myelopathy (e.g., adrenomyeloneuropathy), cerebral, and adrenal. In certain embodiments, the phenotype of X-linked adrenoleukodystrophy is cerebral. In other embodiments, the phenotype of X-linked adrenoleukodystrophy is myelopathy (e.g., moderate to severe myelopathy). In certain other embodiments, the phenotype of X-linked adrenoleukodystrophy is asymptomatic. In yet other embodiments, the phenotype of X-linked adrenoleukodystrophy is Addison disease. In certain embodiments, the phenotype of X-linked adrenoleukodystrophy is olivo-ponto-cerebellar.

The present disclosure features a method of treating a subject having or at risk of developing a disease or condition associated with demyelination, insufficient myelination, or underdevelopment of myelin sheath. The method involves administration of a therapeutically effective amount of sobetirome, or a pharmaceutically acceptable salt thereof.

The present disclosure features a method of inhibiting demyelination of a neuron in a patient that has or is at risk of developing a disease or condition associated with demyelination, insufficient myelination, or underdevelopment of myelin sheath, by contacting the neuron with sobetirome, or a pharmaceutically acceptable salt thereof.

The present disclosure also features a method of promoting myelination of a neuron in a patient that has or is at risk of developing a disease or condition associated with demyelination, insufficient myelination, or underdevelopment of myelin sheath, by contacting the neuron with sobetirome, or a pharmaceutically acceptable salt thereof.

The disease or condition to be treated can be any disease or condition associated with demyelination, insufficient myelination or underdevelopment of myelin sheath. In some embodiments, the disease or condition is multiple sclerosis, a leukodystrophy, a leukoencephalopathy, an idiopathic inflammatory demyelinating disease, or Alzheimer's disease. In some examples in which the disease or condition is multiple sclerosis, the multiple sclerosis is relapsing-remitting multiple sclerosis, primary-progressive multiple sclerosis, secondary-progressive multiple sclerosis, or progressive-relapsing multiple sclerosis.

In some embodiments, the disease or condition is central pontine myelinolysis, acute disseminated encephalomyelitis, Balo concentric sclerosis, Marburg multiple sclerosis, tumefactive multiple sclerosis, diffuse myelinoclastic sclerosis, acute hemorrhagic leukoencephalitis, neuromyelitis optica, a chronic inflammatory demyelinating polyneuropathy, Leber hereditary optic neuropathy, multifocal motor neuropathy, paraproteinemic demyelinating polyneuropathy, tropical spastic paraparesis, a Guillain-Barré syndrome, infantile Refsum disease, adult Refsum disease 1, adult Refsum disease 2, Zellweger syndrome, X-linked adrenoleukodystrophy (X-ALD), metachromatic leukodystrophy, Krabbe disease, Pelizaeus-Merzbacher disease, Canavan disease, Alexander disease, Binswanger's disease, peroneal muscular atrophy, cerebrotendineous xanthomatosis, leukoencephalopathy with vanishing white matter, toxic leukoencephalopathy, van der Knaap disease, progressive multifocal leukoencephalopathy. Marchiafava-Bignami disease or transverse myelitis.

In some examples, the Guillain-Barré syndrome is acute inflammatory demyelinating polyneuropathy.

In some examples, the chronic inflammatory demyelinating polyneuropathy is multifocal acquired demyelinating sensory and motor neuropathy. In some examples, the chronic inflammatory demyelinating polyneuropathy is induced by HIV infection.

In some embodiments, the disease or condition is a chronic axonal neuropathy.

In some embodiments, the disease or condition results from intraventricular hemorrhage, neonatal hypoxia, or acute hypoxemic respiratory failure.

In some embodiments, the disease or condition is cerebral palsy.

In one embodiment, the disease or condition is not X-ALD. In another embodiment, the disease or condition is not multiple sclerosis. In another embodiment, the disease or condition is not cerebral palsy. In another embodiment, the disease or condition is not a leukodystrophy.

In some embodiments of the disclosed method, administration of the sobetirome or pharmaceutically acceptable salt thereof prevents or mitigates at least one symptom of the disease or condition. In some examples, the symptom is a lack of sphincter control, erectile dysfunction, paraparesis, ataxia, adrenocortical insufficiency, progressive neuropathy, paresthesia, dysarthria, dysphagia, clonus, or any combination thereof.

In some embodiments, administration of the sobetirome or pharmaceutically acceptable salt thereof prevents or mitigates damage to central nervous system myelin, peripheral nervous system myelin, adrenal cortex, testicular Leydig cells, or any combination thereof.

In certain embodiments, sobetirome, or a pharmaceutically acceptable salt thereof, is administered orally, parenterally, or topically. In particular embodiments, sobetirome, or a pharmaceutically acceptable salt thereof, is administered orally. In certain embodiments, sobetirome, or a pharmaceutically acceptable salt thereof, is administered enterally. In some embodiments, sobetirome, or a pharmaceutically acceptable salt thereof, is administered buccally, sublingually, sublabially, or by inhalation. In other embodiments, sobetirome, or a pharmaceutically acceptable salt thereof, is administered sublingually. In yet other embodiments, sobetirome, or a pharmaceutically acceptable salt thereof, is administered parenterally. In particular embodiments, sobetirome, or a pharmaceutically acceptable salt thereof, is administered intra-arterially, intravenously, intraventricularly, intramuscularly, subcutaneously, intraspinally, intraorbitally, intracranially or intrathecally.

In some embodiments, the sobetirome or pharmaceutically acceptable salt thereof is administered at a dose of about 1 μg to about 500 μg. In some examples, the sobetirome or pharmaceutically acceptable salt thereof is administered at a dose of about 10 μg to about 100 μg.

In some embodiments, the sobetirome or pharmaceutically acceptable salt thereof is administered daily.

In particular embodiments, the compound is administered to the subject once daily, twice daily, three times daily, once every two days, once weekly, twice weekly, three times weekly, once biweekly, once monthly, or once bimonthly. In certain embodiments, the compound is administered to the subject once daily. In other embodiments, the effective amount is more than 30 μg (e.g., more than 50 μg, such as more than 100 μg). In some embodiments, the effective amount is more than 30 μg (e.g., more than 50 μg, such as more than 100 μg) daily. In certain embodiments, the effective amount is more than 30 μg (e.g., more than 50 μg, such as more than 100 μg) twice daily. In particular embodiments, the effective amount is more than 30 μg (e.g., more than 50 μg, such as more than 100 μg) once weekly. In other embodiments, the effective amount is more than 30 μg (e.g., more than 50 μg, such as more than 100 μg) twice weekly. In certain embodiments, the effective amount is at least 30 μg (e.g., more than 50 μg, such as more than 100 μg) three times weekly. In some embodiments, the effective amount is less than 1 mg (e.g., less than 500 μg, such as less than 200 μg).

In some embodiments, the methods of the present disclosure involve administering a unit dosage form containing from 10 μg to 100 μg of sobetirome, or a pharmaceutically acceptable salt thereof, once, twice or three times per day. In some embodiments, the methods of the present disclosure involve administering a unit dosage form containing from 10 μg to 75 μg of sobetirome, or a pharmaceutically acceptable salt thereof, once, twice or three times per day. In other embodiments, the methods of the present disclosure involve administering a unit dosage form containing from 30 μg to 75 μg of sobetirome, or a pharmaceutically acceptable salt thereof, once, twice or three times per day. In particular embodiments, the methods of the present disclosure involve administering a unit dosage form containing from 10 μg to 50 μg of sobetirome, or a pharmaceutically acceptable salt thereof, once, twice or three times per day. In yet other embodiments, the methods of the present disclosure involve administering a unit dosage form containing from 30 μg to 50 μg of sobetirome, or a pharmaceutically acceptable salt thereof, once, twice or three times per day. In still other embodiments, the methods of the present disclosure involve administering a unit dosage form containing from 50 μg to 75 μg of sobetirome, or a pharmaceutically acceptable salt thereof, once, twice or three times per day.

The present disclosure also features a method of treating a patient having or at risk of developing multiple sclerosis by administering to the patient a therapeutically effective amount of sobetirome, or a pharmaceutically acceptable salt thereof. In one example, provided is a method of treating a patient having or at risk of developing multiple sclerosis, comprising administering to the patient 1 mg/(kg of the weight of said patient)/day of sobetirome, or a pharmaceutically acceptable salt thereof.

Administration of sobetirome and pharmaceutically acceptable salts thereof is further discussed in the section below.

IV. Administration of Sobetirome or Pharmaceutical Compositions Thereof

Sobetirome and pharmaceutically acceptable salts thereof can be administered according to any suitable route of administration for the treatment of a disease or condition associated with demyelination, insufficient myelination, or underdevelopment of myelin sheath. For example, standard routes of administration include oral, parenteral, or topical routes of administration. In particular, the route of administration of sobetirome or a pharmaceutically acceptable salt thereof may be oral (e.g., enteral, buccal, sublingual, sublabial, or by inhalation). Parenteral route of administration of sobetirome, or a pharmaceutical composition thereof, may be, e.g., intra-arterial, intravenous, intraventricular, intramuscular, subcutaneous, intraspinal, intraorbital, or intracranial. Topical route of administration may be, e.g., cutaneous, intranasal, or ophthalmic.

Pharmaceutical compositions comprising sobetirome have been described in the art (see, e.g., U.S. Pat. No. 5,883,294, which is herein incorporated by reference).

Sobetirome and pharmaceutically acceptable salts thereof that are to be administered orally can be formulated as liquids, for example syrups, suspensions or emulsions, or as tablets, capsules or lozenges.

A liquid composition will generally include a suspension or solution of sobetirome or pharmaceutically acceptable salt in a suitable liquid carrier, for example ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

In some cases, a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule. Sobetirome and pharmaceutically acceptable salts thereof to be administered parenterally can be formulated, for example, for intramuscular or intravenous administration.

In some instances, a composition for intramuscular administration contains a suspension or solution of active ingredient in an oil, for example arachis oil or sesame oil. A composition for intravenous administration can include a sterile isotonic aqueous solution containing, for example active ingredient, dextrose, sodium chloride, a co-solvent, for example polyethylene glycol and, optionally, a chelating agent, for example ethylenediamine tetracetic acid and an anti-oxidant, for example, sodium metabisulphite. Alternatively, the solution can be freeze dried and then reconstituted with a suitable solvent just prior to administration.

Sobetirome and pharmaceutically acceptable salts thereof for rectal administration can be formulated as suppositories. A typical suppository formulation will generally include active ingredient with a binding and/or lubricating agent such as a gelatin or cocoa butter or other low melting vegetable or synthetic wax or fat.

Sobetirome and pharmaceutically acceptable salts thereof to be administered topically can be formulated as transdermal compositions. Such compositions include, for example, a backing, active compound reservoir, a control membrane, liner and contact adhesive.

Non-limiting examples of formulations for buccal, sublingual, and/or sublabial administration may be found in U.S. Pre-grant Publication No. 2012/0058962, U.S. Pre-grant Publication No. 2013/0225626, U.S. Pre-grant Publication No. 2009/0117054, and U.S. Pat. No. 8,252,329; the disclosure of each of which is incorporated herein by reference.

For buccal, sublingual, or sublabial administration, the compositions may take the form of tablets, lozenges, etc. formulated in a conventional manner, as described for oral dosage forms. In some embodiments, the formulation for buccal, sublingual, or sublabial administration includes one or more of taste masking agents, enhancers, complexing agents, and other described above pharmaceutically acceptable excipients and carriers.

Taste masking agents include, for example, taste receptor blockers, compounds which mask the chalkiness, grittiness, dryness, and/or astringent taste properties of an active compound, compounds which reduce throat catch as well as compounds which add a flavor. A taste receptor blocker used in the formulation of the present disclosure may include Kyron T-134, a glycoprotein extract called miraculin from the fruit of the plant *synsepalum dulcifcum*, ethyl cellulose, hydroxypropyl methylcellulose, arginine, sodium carbonate, sodium bicarbonate, gustducin blockers and mixtures thereof. Compounds which mask the chalkiness, grittiness, dryness and/or astringent taste properties of an active compound include those of a natural or synthetic fatty type or other flavorant such as cocoa, chocolate (e.g., mint chocolate), cocoa butter, milk fractions, vanillin butter fat, egg or egg white, peppermint oil, wintergreen oil, spearmint oil, and similar oils. Compounds which reduce throat catch include combinations of high and low solubility acids. For example, high solubility acids suitable for use here include amino acids (e.g., alanine, arginine etc.), glutaric, ascorbic, malic, oxalic, tartaric, malonic, acetic, citric acids and mixtures thereof. Low solubility acids suitable for use include oleic, stearic and aspartic acids plus certain amino acids such as glutamic acid, glutamine, histidine, isoleucine, leucine, methionine, phenylalanine, serine, tryptophan, tyrosine, valine and fumaric acid. Actual amounts used will vary depending on the amount of throat catch or burn exhibited by the active used but will generally be in the range of 1 to 40%. Flavoring agents include sweeteners and flavors. Examples of suitable sweeteners and flavors include mannitol, sorbitol, maltitol, lactitol, isomaltitol, erythritol, xylitol, sucrose, ammonium glycyrrhizinate, mango aroma, black cherry aroma, sodium citrate, colloidal silicon dioxide, sucralose; zinc gluconate; ethyl maltitol; glycine; acesulfame-K; aspartame; saccharin; acesulfam K, neohesperidin DC, thaumatin, stevioside, fructose; xylitol; honey; honey extracts; corn syrup, golden syrup, misri, spray dried licorice root; glycerrhizine; dextrose; sodium gluconate; stevia powder; glucono delta-lactone; ethyl vanillin; vanillin; normal and high-potency sweeteners or syrups or salts thereof and mixtures thereof. Other examples of appropriate flavoring agents include coffee extract, mint; lamiacea extracts; citrus extracts; almond oil; babassu oil; borage oil; blackcurrant seed oil; canola oil; castor oil; coconut oil; corn oil; cottonseed oil; evening primrose oil; grape seed oil; groundnut oil; mustard seed oil; olive oil; palm oil; palm kernel oil; peanut oil; grapeseed oil; sunflower oil; sesame oil; shark liver oil; soybean oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; soy oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; glyceryl tricaprylate/caprate/stearate; saturated polyglycolized glycerides; linoleic glycerides; caprylic/capric glycerides; modified triglycerides; fractionated triglycerides; safrole, citric acid, d-limonene, malic acid, and phosphoric acid or salts and/or mixtures thereof.

Enhancers are the agents that increase membrane permeability and/or increase the solubility of a particular active compound. Both issues can be pivotal to the properties of the formulation. An enhancer may be a chelator, a surfactant, a membrane-disrupting compound, a fatty or other acid; a non-surfactant, such as an unsaturated cyclic urea. A chelator may be, e.g., EDTA, citric acid, sodium salicylate, or a methoxysalicylate. A surfactant may be, e.g., sodium lauryl sulphate, polyoxyethylene, POE-9-laurylether, POE-20-cetylether, benzalkonium chloride, 23-lauryl ether, cetylpyridinium chloride, cetyltrimethyl ammonium bromide, or an amphoteric or a cationic surfactant. A membrane-disrupting compound may be, e.g., a powdered alcohol (such as, menthol) or a compound used as lipophilic enhancer. Fatty and other acids include, e.g., oleic acid, capric acid, lauric acid, lauric acid/propylene glycol, methyloleate, yso-phosphatidylcholine, and phosphatidylcholine. Other enhancers that may be used in buccal, sublingual, and sublabial formulations of the present disclosure include, e.g., lysalbinic acid, glycosaminoglycans, aprotinin, azone, cyclodextrin, dextran sulfate, curcumin, menthol, polysorbate 80, sulfoxides, various alkyl glycosides, chitosan-4-thiobutylamide, chitosan-4-thiobutylamide/GSH, chitosan-cysteine, chitosan-(85% degree N-deacetylation), poly(acrylic acid)-homocysteine, polycarbophil-cysteine, polycarbophil-cysteine/GSH, chitosan-4-thioethylamide/GSH, chitosan-4-thioglycholic acid, hyaluronic acid, propanolol hydrochloride, bile salts, sodium glycocholate, sodium deoxycholate, sodium taurocholate, sodium glycodeoxycholate, and sodium taurodeoxycholate.

Buffering materials can be both used to increase solubility and enhance adsorption of active compounds. Examples of suitable buffering materials or antacids suitable for use herein comprise any relatively water soluble antacid acceptable to the Food & Drug Administration, such as aluminum carbonate, aluminum hydroxide (or as aluminum hydroxide-hexitol stabilized polymer, aluminum hydroxide-magnesium hydroxide co-dried gel, aluminum hydroxide-magnesium trisilicate codried gel, aluminum hydroxide-sucrose powder hydrated), aluminum phosphate, aluminum hydroxyl carbonate, dihydroxyaluminum sodium carbonate, aluminum magnesium glycinate, dihydroxyaluminum aminoacetate, dihydroxyaluminum aminoacetic acid, bismuth aluminate, bismuth carbonate, bismuth subcarbonate, bismuth subgallate, bismuth subnitrate, calcium carbonate, calcium phosphate, hydrated magnesium aluminate activated sulfate, magnesium aluminate, magnesium aluminosilicates, magnesium carbonate, magnesium glycinate, magnesium hydroxide, magnesium oxide, and magnesium trisilicate, and/or mixtures thereof. Preferred buffering materials or antacids include aluminum hydroxide, calcium carbonate, magnesium carbonate and mixtures thereof, as well as magnesium hydroxide. Many of these compounds have the advantage of also being taste masking agents particularly useful for addressing throat catch.

The selection of the other excipients, such as permeation enhancers, disintegrants, masking agents, binders, flavors, sweeteners and taste-masking agents, is specifically matched to the active depending on the predetermined pharmacokinetic profile and/or organoleptic outcome.

Liquid drug formulations suitable for use with nebulizers and liquid spray devices and electrohydrodynamic (EHD) aerosol devices will typically include sobetirome or a pharmaceutically acceptable salt thereof with a pharmaceutically acceptable carrier. Preferably, the pharmaceutically acceptable carrier is a liquid, e.g., alcohol, water, polyethylene glycol, or a perfluorocarbon. Optionally, another material may be added to alter the aerosol properties of the solution or suspension. Desirably, this material is liquid, e.g., an alcohol, glycol, polyglycol, or a fatty acid. Other methods of formulating liquid drug solutions or suspension suitable for use in aerosol devices are known to those of skill in the art (see, e.g., U.S. Pat. No. 5,112,598 and U.S. Pat. No. 5,556,611, each of which is herein incorporated by reference).

The dose and dosing schedule for administration of sobetirome (or a pharmaceutically acceptable salt thereof) can vary and is determined in part by the severity of the disease, and the age, weight and general health of the patient. In some embodiments, the composition is administered daily. In other embodiments the composition is administered more than once a day, such as twice a day, three time a day or four times a day. In yet other embodiments, the composition is administered less than once a day, such as every other day, every three days or once a week.

In some embodiments, the dose of sobetirome (or a pharmaceutically acceptable salt thereof) is about 1 µg to about 500 µg (e.g., twice daily, once daily, twice weekly, or once weekly), such as about 5 µg to about 250 µg (e.g., twice daily, once daily, twice weekly, or once weekly), about 10 µg to about 100 µg (e.g., twice daily, once daily, twice weekly, or once weekly), about 25 µg to about 75 µg (e.g., twice daily, once daily, twice weekly, or once weekly), or about 50 µg to about 100 µg (e.g., twice daily, once daily, twice weekly, or once weekly). In particular examples, the dose of sobetirome (or a pharmaceutically acceptable salt thereof) is about 1, 5, 10, 15, 20, 25, 30, 40, 50, 60, 70, 75, 100, 125, 150, 200, 250, 300, 350, 400, 450 or 500 µg (e.g., twice daily, once daily, twice weekly, or once weekly).

The following examples are provided to illustrate certain particular features and/or embodiments. These examples should not be construed to limit the disclosure to the particular features or embodiments described.

EXAMPLES

Example 1: Use of Sobetirome for the Treatment of Multiple Sclerosis (MS)

Figure 1:
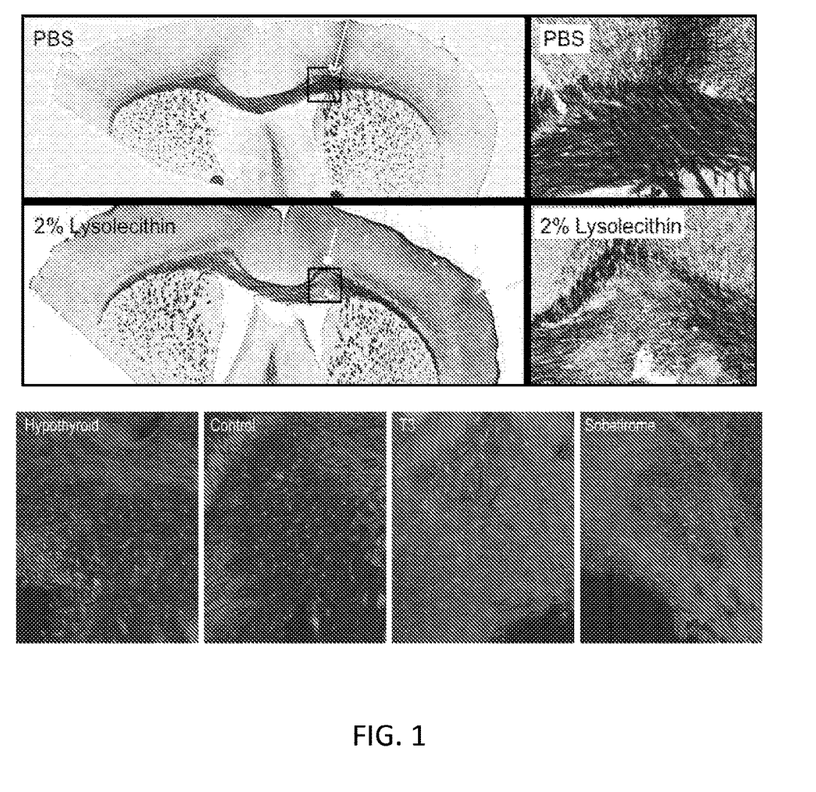

This example describes the finding that treatment with sobetirome decreased demyelination in two different animal models of MS.
Chronic Demyelination Contributes to Disability and Progressive Impairment in MS In MS, inflammatory cells induce multifocal demyelination and variable axonal degeneration in the CNS, referred to as MS plaques. Consequently, people with MS develop a variety of neurologic deficits, including paralysis, gait impairment, cognitive dysfunction, loss of sensation, and impaired vision. While remyelination occurs spontaneously as part of the natural repair process in MS, it is incomplete and tends to become ineffective as the disease progresses. Failure of remyelination leads to chronically demyelinated axons that lose their ability to conduct axon potentials normally resulting in neurologic dysfunction. Importantly, chronic demyelination may contribute to the pathogenesis of progressive axonal degeneration, which is a major cause of permanent disability.
Remyelination Occurs Early in MS but Fails as the Disease Progresses Spontaneous remyelination occurs in MS and can be quite extensive. More commonly, remyelination occurs at the edges of typical demyelinated plaques and tends to become less robust with longer disease duration. Why remyelination fails is uncertain. OPC are present near or in demyelinated plaques but for uncertain reasons do not differentiate into OL and form myelin. It is possible that the demyelinated axons fail to signal OPC properly. Another theory is that the astrocytic "scar" that develops in chronic MS plaques inhibits OPC migration and differentiation, possibly through the presence of high molecular weight hyaluronic acid. It is also possible that activated microglia and macrophages within and near the MS plaques release soluble factors that inhibit OPC differentiation.
Animal Models for Studying Remyelination Several animal models are in use to assess the effectiveness of therapies to promote remyelination, including models that use a toxin (lysolecithin, ethidium bromide, or cuprizone) to induce demyelination; EAE; and Theiler's murine encephalomyelitis. In both the EAE and Theiler's models, demyelination is immune mediated. In this example, one toxin model (lysolecithin) and one immune-mediated model (EAE) are used to evaluate sobetirome.
Sobetirome Reduces Demyelination in the Lysolecithin Toxin Model of Focal Demyelination This study revealed that sobetirome can alter demyelination in this focal demyelination model (FIG. 1). Lysolecithin was injected into the corpus callosum using stereotactic equipment at the x, y, z coordinates of +1.000, +1.050, and +2.000 mm from the Bregma point using a beveled needle with the bevel facing caudally. To minimize trauma, 2 µL of 2% lysolecithin or 2 µL of PBS was injected over four minutes using a micropump injector and the beveled needle was held in place for five minutes before withdrawal. Brains were harvested 8 days later and fixed in paraformaldehyde. Free-floating slices of 30 µm were sectioned with a vibratome and stained with BlackGold® to detect myelin. In lysolecithin-injected (but not PBS-injected) C57BL/6 mice, demyelination was observed in 6-8 serial sections in the corpus callosum (FIG. 1).

The initial experiment sought to determine how hypothyroidism, hyperthyroidism induced with high doses of T3, and administration of sobetirome initiated before lysolecithin injection affected the extent of demyelination 8 days after lysolecithin injection. To induce hypothyroidism, mice were given 0.1% methimazole and 0.2% potassium perchlorate in the drinking water for two weeks before lysolecithin injection; oral administration of these reagents inhibits the production of thyroid hormone and induces hypothyroidism. Both T3 (0.4 mg/kg/day) and sobetirome (1.0 mg/kg/day) were administered daily by i.p. injection starting 7 days before and for 8 days after lysolecithin injection. Euthyroid control mice and hypothyroid mice received daily i.p. injections of vehicle for 7 days prior and 8 days after lysolecithin injection. Eight days after administration of lysolecithin (FIG. 1), mice receiving sobetirome and T3 had much smaller areas of demyelination than those receiving vehicle. Hypothyroid mice had much larger areas of demyelination that euthyroid mice. These initial experiments show that thyroid status affects demyelination in the lysolecithin model, which has not been previously demonstrated, and that sobetirome decreases demyelination in this model.

Sobetirome Decreases Demyelination in EAE

Figure 2:
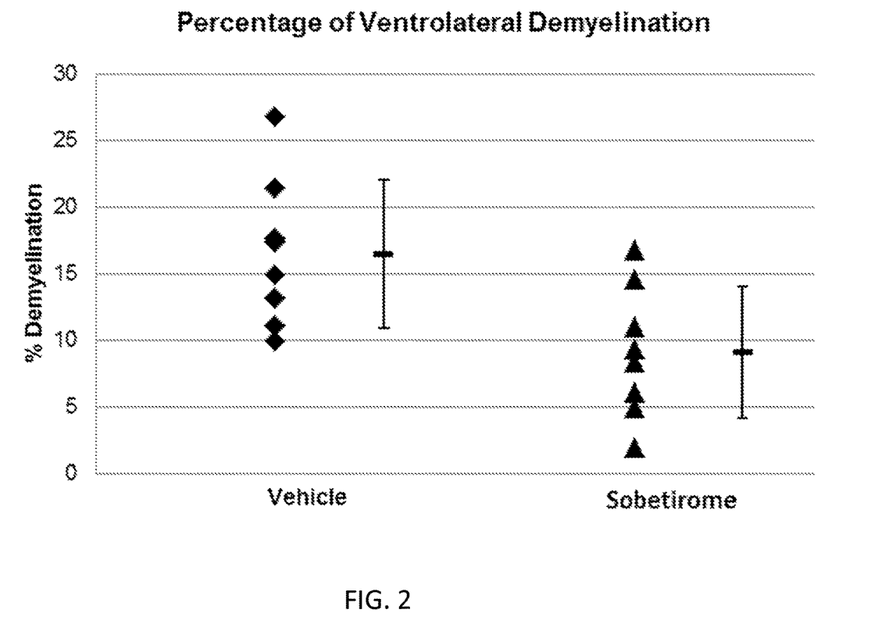
FIG. 2: Sobetirome reduces demyelination in mice with EAE. The dot plot displays the mean percentage area of damage in the ventrolateral white matter of C57BL/6 mice after 11 days of treatment with sobetirome and vehicle. EAE was induced in female mice with MOG 35-55 peptide. On day 17 post immunization, mice were randomized based on their EAE scores and daily i.p. injections of sobetirome (n=8) or vehicle (n=8) were started. Mice were euthanized after 11 days of treatment and spinal cords were prepared for histological evaluation. The mean percentage of ventrolateral demyelination for vehicle treated mice was 17.25 (SD+/−7.09) and 9.11 (SD+/−4.96) for sobetirome (p<0.01).
Figure 3A:
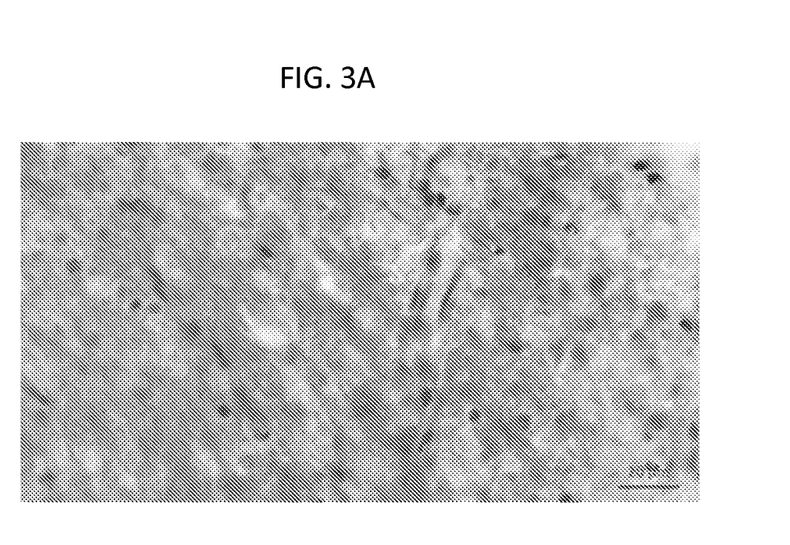
FIGS. 3A-3D: Sobetirome prevents demyelination and axonal loss. Representative Black gold II (FIGS. 3A-3B) and toluidine blue (FIGS. 3B-3C) images from lumbar and thoracic EAE ventral spinal cord respectively. Sobetirome treated (FIGS. 3A and 3C) and vehicle (FIGS. 3B and 3D). Demyelination is clearly visible in a vehicle-treated mouse but not in a sobetirome-treated mouse. Arrows show unstable myelin; arrowheads show degenerating axon. Scale bar=20 microns.
Figure 3B:
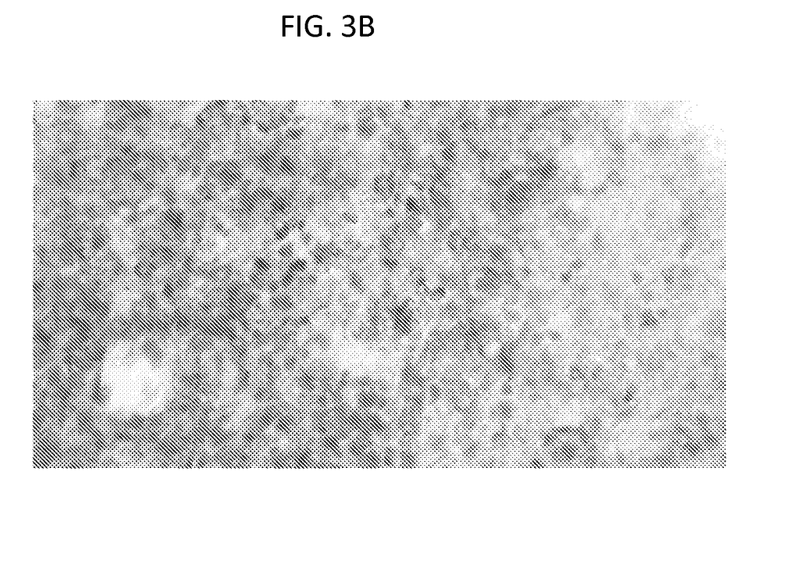
Figure 3C:
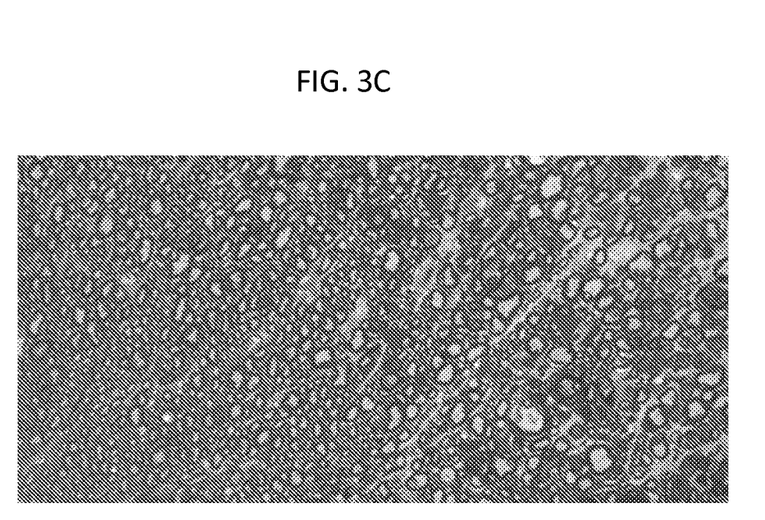
Figure 3D:
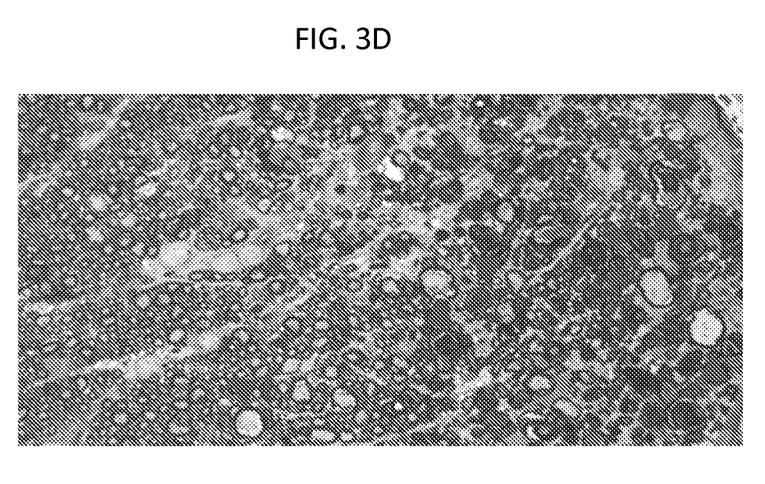

This study was performed to assess the effects of sobetirome on EAE in C57BL/6 female mice immunized with MOG 35-55 peptide. Seventeen days after immunization, at peak of clinical disease, mice were randomized to receive daily injections of sobetirome (1 mg/kg/day) or vehicle. After 11 days of treatment, mice were euthanized and processed for histologic examination. EAE clinical scores for the two groups did not differ significantly. This is because the degree of inflammation within the spinal cords was similar between the two groups (Table 1) and much of the short term paralysis that occurs in EAE is secondary to effects of inflammation on neural function. However, the lateral columns of the lumbosacral cord had significantly less demyelination in the mice receiving sobetirome compared with those receiving vehicle (p<0.01; FIG. 2). Much of the effect appears related to protection of axons and myelin from damage (FIG. 3). Thus, sobetirome has a neuroprotective effect that decreases axonal damage and demyelination.

TABLE 1

Immunofluorescent staining of lumbosacral spinal cord sections stained for a macrophage marker (CD11b) and a T cell marker (CD4)

| ID | Group | # | % CD11b Staining | % CD4 Staining |
|---|---|---|---|---|
| 1339 and 1340 | Sobetirome | 8 | 5.76 | 1.24 |
| 1342 | Vehicle | 4 | 3.89 | 1.01 |

Summary of Animal Model Data

Sobetirome decreased demyelination in the lysolecithin focal demyelination model. This model is widely used to study mechanisms of myelin repair and to assess the therapeutic potential of drugs and other therapies to promote remyelination in multiple sclerosis. Sobetirome also decreased demyelination and axonal injury in experimental autoimmune encephalomyelitis (EAE), the classic model of multiple sclerosis. These studies demonstrate that Sobetirome is effective in promoting remyelination and serves as a neuroprotectant in multiple sclerosis.

Example 2: Sobetirome in an Animal Mode of Neonatal Hypoxia

Chronic neonatal hypoxia is a clinically relevant model of premature brain injury caused by insufficient gas exchange from poor lung development. This hypoxic state is a significant contributor to diffuse white matter injury (DWMI), which is common in infants born prematurely. Chronic hypoxia can cause myelination abnormalities. A mouse model of chronic hypoxia has been previously described (Scafidi et al., Nature doi: 10.1038/nature12880 [Epub ahead of print], Dec. 25, 2013). This model can be used to evaluate the effect of sobetirome on oligodendrocyte regeneration and remyelination following hypoxia.

Mice are randomly selected to undergo hypoxic rearing or to serve as normoxic controls. Hypoxic mice are placed in a sealed chamber maintaining $O_2$ concentration at 10.5% by displacement with $N_2$ as described previously (Raymond et al., J Neurosci 31:17864-17871, 2011; Bi et al., J Neurosci 31:9205-9221, 2011; Jablonska et al., J Neurosci 32:14775-14793, 2012). Hypoxia is initiated at post-natal day (P)3 and continues for 8 days until P11. This time frame in rodent white matter oligodendrocyte development reproduces changes that occur at 23-40 weeks of gestation in the human brain (Back et al., J Neurosci 21:1302-1312, 2001). Age- and strain-matched mice serve as normoxic controls.

Hypoxic mice and normoxic control mice are randomized to receive daily injections of sobetirome (1 mg/kg/day) or vehicle. In some examples, administration of sobetirome (or vehicle) is initiated at P11. In other examples, treatment is initiated at P3 or any time between P3 and P11. Multiple daily doses of sobetirome (and vehicle) can be administered. Following the desired course of treatment, mice are sacrificed and brain sections are prepared and processed to evaluate myelin thickness and the number of oligodendrocyte precursor cells in the white matter as described (Scafidi et al., Nature doi: 10.1038/nature12880 [Epub ahead of print], Dec. 25, 2013).

All publications, patents, and patent applications mentioned in the above specification are hereby incorporated by reference. Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

The invention claimed is:

1. A method of treating a subject having inflammation/demyelination at one or more sites in the central nervous system at risk of developing or diagnosed with multiple sclerosis, said method comprising orally administering to the subject a therapeutically effective amount of sobetirome or a pharmaceutically acceptable salt thereof.

2. The method of claim 1, wherein the multiple sclerosis is relapsing-remitting multiple sclerosis, primary-progressive multiple sclerosis, secondary-progressive multiple sclerosis, or progressive-relapsing multiple sclerosis.

3. The method of claim 1, wherein administration of the sobetirome or pharmaceutically acceptable salt thereof prevents, mitigates, or slows the progression of at least one symptom of the multiple sclerosis.

4. The method of claim 3, wherein the symptom is a lack of sphincter control, erectile dysfunction, paraparesis, ataxia, adrenocortical insufficiency, progressive neuropathy, paresthesia, dysarthria, dysphagia, clonus, or any combination thereof.

5. The method of claim 1, wherein the sobetirome or pharmaceutically acceptable salt thereof is administered at a dose of about 1 µg to about 500 µg daily.

6. A method of treating a patient having inflammation/demyelination at one or more sites in the central nervous system at risk of developing or diagnosed with multiple sclerosis, comprising administering to the patient 1 mg/kg/day of sobetirome, or a pharmaceutically acceptable salt thereof.

* * * * *

UNITED STATES PATENT AND TRADEMARK OFFICE
CERTIFICATE OF CORRECTION

PATENT NO. : 10,226,438 B2
APPLICATION NO. : 14/888577
DATED : March 12, 2019
INVENTOR(S) : Thomas S. Scanlan et al.

Page 1 of 1

It is certified that error appears in the above-identified patent and that said Letters Patent is hereby corrected as shown below:

In the Specification

Please delete the paragraph under the heading ACKNOWLEDGEMENT OF GOVERNMENT SUPPORT from Column 1, Lines 18-21 that appears as:
"This invention was made with government support under grant number DK-52798 awarded by the National Institutes of Health. The government has certain rights in the invention."

And replace it with the passage below:
-- This invention was made with government support under DK052798 and DK007680 awarded by the National Institutes of Health. The government has certain rights in the invention. --

Signed and Sealed this
Ninth Day of July, 2019

Andrei Iancu
*Director of the United States Patent and Trademark Office*